ized Ascorbic Acid,
United States Patent [19]

Mitchnick et al.

[11] Patent Number: 6,103,267
[45] Date of Patent: Aug. 15, 2000

[54] STABILIZED ASCORBIC ACID, COMPOSITION, AND METHOD OF USE

[75] Inventors: Mark A. Mitchnick, East Hampton, N.Y.; Garry Gwozdz, Nazareth, Pa.

[73] Assignee: SunSmart, Inc., Wainscott, N.Y.

[21] Appl. No.: 09/122,828

[22] Filed: Jul. 27, 1998

[51] Int. Cl.[7] .............................. A61K 9/10; A61K 7/00; A61K 31/375
[52] U.S. Cl. ...................... 424/489; 424/401; 424/70.19; 514/474; 514/880; 514/937; 514/938
[58] Field of Search ...................................... 424/401, 489, 424/494, 497, 498, 70.11, 70.12, 70.16, 70.19; 514/474, 880, 937, 938; 924/70.21, 70.22

[56] References Cited

U.S. PATENT DOCUMENTS

| | | | |
|---|---|---|---|
| 3,958,017 | 5/1976 | Morse et al. | 426/72 |
| 4,983,382 | 1/1991 | Wilmott et al. | 424/62 |
| 5,114,972 | 5/1992 | Ohnishi | 514/530 |
| 5,140,043 | 8/1992 | Darr et al. | 514/474 |
| 5,200,172 | 4/1993 | Kamen et al. | 424/64 |
| 5,280,092 | 1/1994 | Chuang | 526/201 |
| 5,281,196 | 1/1994 | Sultenfuss | 604/20 |
| 5,308,621 | 5/1994 | Taylor et al. | 424/401 |
| 5,376,361 | 12/1994 | Perricone | 424/59 |
| 5,409,693 | 4/1995 | Perricone | 424/59 |
| 5,470,874 | 11/1995 | Lerner | 514/474 |
| 5,516,793 | 5/1996 | Duffy | 514/474 |
| 5,552,446 | 9/1996 | Candau et al. | 514/772.4 |
| 5,574,063 | 11/1996 | Perricone | 514/474 |
| 5,607,968 | 3/1997 | Ptchelintsev | 514/474 |
| 5,656,280 | 8/1997 | Herb et al. | 424/401 |
| 5,736,567 | 4/1998 | Cantin et al. | 514/474 |

Primary Examiner—Thurman K. Page
Assistant Examiner—Lakshmi Channavajjala
Attorney, Agent, or Firm—Schwegman, Lundberg, Woessner & Kluth, P.A.

[57] ABSTRACT

A dispersion for carrying at least one water-soluble material or water-dispersible material (especially ascorbic acid, Vitamin C) in a relatively stable form is described, the dispersion comprising an oil phase containing particles comprising water-soluble polymer, water-soluble material or water-dispersible material (ascorbic acid), and water. The dispersion preferably comprises particles which have number average diameter dimensions of less than 2 microns, more preferably less than 1 micron. The dispersion may comprise oil components such as, for example only, a mineral oil, silicone oil, or cosmetic oil. A method of forming a dispersion of solid particles which comprise water-soluble material or water-dispersible material (e.g., ascorbic acid) in a water-soluble polymer may comprise the steps of:

a) forming a first solution of the water-soluble material or water-dispersible material (ascorbic acid), water and a water-soluble polymer, b) mixing the first solution with a second solution of a water in a surface active agent having an HLB of less than 12 or less than 10 and oil, c) dispersing the first solution and the second solution to form a mixture of the first solution and second solution, and d) cooling the mixture, solidifying the first solution to form particles dispersed in said oil. This method may have the emulsifying done at a temperature above 40° C., preferably above 50° C., more preferably above 55° C.

33 Claims, No Drawings

STABILIZED ASCORBIC ACID, COMPOSITION, AND METHOD OF USE

BACKGROUND OF THE INVENTION

1. Field of the Invention

The present invention relates to a non-aqueous dispersion of hydrophilic particles that contain stabilized ascorbic acid, which is useful in the cosmetic, dermatological and/or veterinary fields, and methods for using these dispersion in the cosmetic treatment of the skin as well as for the preparation of a cream or ointment intended for the dermatological treatment of the skin and/or for veterinary treatment.

2. Background of the Art

Workers have long sought to stabilize ascorbic acid, or vitamin C, in suitable pharmaceutical forms to enable wider use of its beneficial properties.

Ascorbic acid has many known biological functions, such as the stimulation of collagen synthesis, the strengthening of skin tissues against external attack (UV radiation, pollution), reduction in loss of pigmentation, activity against free radicals and compensation for vitamin B deficiency. Some of these beneficial properties have been reported in particular by England and Seifter in the article "The bio-chemical functions of ascorbic acid" published in *Ann. Rev. Nutri.*, 1986; 6, pp. 365–406.

However, the chemical structure (alpha-keto lactone) of ascorbic acid is very sensitive to the influence of environmental parameters such as light, oxygen and water (due to ascorbic acid's pH sensitivity and due to the presence of trace metals in water which may form chelates with the ascorbic acid). A heretofore unavoidable degradation of ascorbic acid in aqueous solution therefor occurs over time.

This problem has been addressed in a variety of ways in the art. For example, to reduce or delay the degradation of ascorbic acid in solution, U.S. Pat. No. 5,140,043 recommends stabilization by introducing ascorbic acid into aqueous-alcoholic solutions, formed of at least 80% water and having a pH below 3.5.

The high acidity of these solutions reduces or negates their utility in the cosmetic and/or pharmaceutical field. Repeated applications of such solutions could disrupt the equilibrium of the skin and might irritate, or even burn, the skin.

B. R. Hajratwala, in "Stability of Ascorbic Acid", published in the Revue Sciences Pharmacentiques on Mar., 15, 1905, teaches that ascorbic acid may be stabilized as an acidic aqueous solution by adding a surface-active agent which is an oxyethylenated sorbitan ester. In particular, Hajratwala states that a pH=3.4 and 25° C., the addition of this agent reduced the rate of oxidation, and thus the rate of degradation, of ascorbic acid in solution. Hajratwala also teaches the use of a chelating agent (e.g., for monovalent cations) such as ethylenediaminetetraacetic acid (EDTA) and packaging under nitrogen, in the absence of light, to enhance the stability of an aqueous ascorbic acid solution.

Again, however, such an acidic aqueous solution if applied to the skin, would have the same drawbacks as those described above for acidic aqueous-alcoholic solutions. Furthermore, the stabilization provided would be insufficient.

Other ways of stabilizing ascorbic acid have been proposed, in particular by a coating technique (FR-A-1,600, 826) or by granulation of ascorbic acid (JP-A-53-127,819) for the agriculture-foods industry.

However, these techniques tend to be expensive and may damage the ascorbic acid, for example during heating suggested for some of the processing, and/or may lead to compositions of poor cosmetic acceptability, as in the case of granules.

FR-A-1,489,249 discloses the use of metal salts of phosphorylated ascorbic acid, in particular magnesium ascorbylphosphate, in cosmetic compositions. The latter compound has an activity close to that of ascorbic acid, from which it is derived, but it has certain drawbacks which render its use on the skin less desirable. In particular, since magnesium ascorbylphosphate is only stable at basic pH (pH 8 to pH 9), it must be incorporated into a basic composition which may be an irritant to the skin (the pH of which is about 5.5).

U.S. Pat. No. 5,308,621 describes a composition for use in the transdermal administration of ascorbic acid (vitamin C) comprising a pharmaceutically acceptable carrier having 1 to 60% by weight of ascorbic acid in suspension within the carrier, the suspension of ascorbic acid comprising fine particles of ascorbic acid sized below 20 microns, preferably between 2 and 10 microns. The composition is formed by mixing the ascorbic acid into the carrier, heating up the mixture to dissolve the vitamin C, then cooling the solution to precipitate the vitamin C as small crystals. Typical carriers include polyhydric alcohols, alcohols, polyalkylene glycols, ointment bases such as petroleum jelly and lanolin, and the like. The preferred compositions are essentially water free, with less than about 0.5% by weight water.

U.S. Pat. No. 5,409,693 describes the use of ascorbic acid in the form of a fat-soluble fatty acid ester to treat sunburn and prevent sunburn damage to skin. The ascorbic acid derivative may be dispersed or dissolved in a pharmaceutically acceptable carrier.

U.S. Pat. No. 5,552,446 describes the use of a water in oil emulsion containing stabilized ascorbic acid. The emulsion contains an aqueous phase with a pH which is at most 3.5 (an acidic phase) in combination with particular emulsifying agents selected from dimethiconecopolyol or alkyldimethiconecopolyol. The stabilized ascorbic acid in the emulsion is suggested for use in the cosmetic, dermatological and/or veterinarian fields. The emulsion is taught to contain at least 60% by weight of water to prevent release of oil from the emulsion which would destabilize the emulsion. The ascorbic acid content is 0.5 to 5% by weight. With a maximum of 5% ascorbic acid it is limited because higher concentrations are desirable (see U.S. Pat. No. 5,140,043; column 3; line 22).

Consequently, none of the previous proposals have made it possible to overcome the technical problem associated with the instability of ascorbic acid in solution, in a pharmaceutical form which is suitable for the cosmetic and/or dermatological fields and at a cost which is compatible with industrial requirements.

BRIEF DESCRIPTION OF THE INVENTION

The present invention provides a method for providing a stable composition for use in various fields of technology, including, but not limited to the cosmetic or medical fields. The stable compositions may comprise hydrophilic agents, water-dispersible or water-soluble active ingredients, such as for example, vitamins (especially Vitamin C), anti-inflammatory agents, anesthetics, enzymes in an aqueous suspension (or dispersion) which is microdispersed within a continuous oleophilic phase. The ingredient must be contained in at least the amount needed to be effective, which in the case of Vitamin C is at least 5% (e.g., at least 5.5% or at least 6.0% by weight), preferably more than 7% or more than 8.5%, and most preferably at least 10% (e.g., up to 40, 50, 60 or 75%) by weight of the dispersion/suspension as the water-soluble material or water-dispersible material, such as the Vitamin C. Other materials may be present in lower concentrations within the dispersed phase, if they are needed or useful in lower amounts for measurable activity (e.g., at least 0.5%, at least 1% or more). A low HLB surface active agent or tenside may also assist the system in a continuous non-aqueous (e.g., lipophilic, hydrophobic or oil) phase. Also present within the composition is a water-soluble/water-dispersible polymer and oil. A final product may comprise a dispersion of particles (e.g., comprising a mixture or solution of the water-soluble material or water-dispersible material such as ascorbic acid, water and polymer) in a continuous non-aqueous phase. The particles (comprising a homogeneous mix within the particles) tend to be stable against settling, creaming, separation, agglomeration and flocculation. At the same time, the dispersion provides enhanced stability against chemical oxidation or breakdown of the water-soluble material or water-dispersible material such as ascorbic acid, which can be apparent by visual observation of yellowing or browning of aqueous solutions of ascorbic acid. This improved stability can be evidenced over conventional aqueous solutions of ascorbic acid at both room temperature and elevated temperature, without special packaging (e.g., air tight containers) or restricted atmospheres (e.g., inert gas environments).

DETAILED DESCRIPTION OF THE INVENTION

A composition which is capable of providing cosmetically or medically useful amounts of a water-soluble material or water-dispersible material such as Vitamin C is provided. Additional or alternative water-soluble or water-dispersible materials may include vitamins, anti-inflammatory agents, anesthetics, analgesics, enzymes, fragrances, UV absorbers (sunscreen agents), antiperspirants, deodorants, pigments, dyes, hydroxy acids (e.g., alpha hydroxy acids, beta hydroxy acids), skin lightening agents, emollients, medications, antibiotics, antifungal agents, repellants, attractants (e.g., pheromones), and the like. The composition comprises a microdispersion of particles within an oleophilic phase. The particles comprise at least the water-soluble material or water-dispersible material such as Vitamin C, water and polymer, with the particles distributed within a continuous oleophilic phase. Within the composition is a low HLB surface active agent (which may be present in the aqueous phase, the oleophilic phase, or both phases within the composition). The composition generally may be formed by any method which disperses the aqueous (or water) phase containing the water-soluble material or water-dispersible material such as the Vitamin C and polymer within a continuous phase of oleophilic liquid. A simple and preferred process comprises forming a solution of low HLB surface active agents and oil. After dissolving a water-soluble (water-dispersible) polymer in water (e.g., deionized or highly deionized water is preferred), preferably at an elevated temperature, e.g., above 20° C., preferably at about 40–70° C., most preferably between 55–65° C., the solutions are mixed and the water-soluble material or water-dispersible material (e.g., the Vitamin C) is added to dissolution. The water soluble phase is dispersed into the oil phase by agitation, such as with an ultrasonic processor, high pressure homogenizer, colloid mill, or high sheer mixer until small, fairly uniform size particles are formed. The dispersion is then cooled to at least room temperature to form the final dispersion of aqueous phase particles within the continuous oil phase. The fairly uniform particles forms within the oil phase should be less than 2 microns, preferably have number average diameters of less than 1 micron, more preferably have number average diameters of less than 0.75 microns, and most preferably have number average diameters of between 0.05 and 0.75 microns, with 0.1 to 0.75 microns being particularly preferred.

The assignment of numerical values for hydrophilic-lipophilic balance (HLB) is based upon the effects of chemical groups within a molecule. This is a well known and accepted basis of determining characteristics of materials as shown by A. W. Adamson, "Physical Chemistry of Surfactants," 2d Edition (Interscience Publishers, New York, 1967), pp. 520–522. A detailed description of HLB is also provided in M. J. Schnick, "Surfactants Science Series," Vol. 1, Nonionic Surfactants, Chapter 18 (M. Dekker, Inc., New York 1967); J. Soc. Cosm. Chem., Vol. 5, pp. 249–256 (1954); and M. L. Prince in M. G. DeNavarre, "The Chemistry and Manufacture of Cosmetics," Vol. III, 2d Edition (Continental Press, Orlando, 1975), pp. 25–37. Quantitative Relationships Between Ester Structure And Emulsion Properties," J. Dispersion Science And Technology, 13(3), 315–336 (1992); P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et al., "Efficiency and usability of silicone surfactants in emulsions," Provisional Communication, International Journal of Cosmetic Science, 12, 135–139 (1990); and D. G. Krzysik et al., "A New Silicone Emulsifier For Water-in-Oil Systems," Drug and Cosmetic Industry, vol. 146(4) pp. 28–81 (April 1990); which have already been incorporated by reference herein in their entirety.

A dispersion is described comprising a non-aqueous phase containing particles comprising water-soluble polymer, ascorbic acid, and water. The dispersion preferably comprises particles which have number average diameter dimensions of less than 2 microns, more preferably less than 1 micron. The dispersion may comprise oil components such as, for example only, a mineral oil, or cosmetic oil. The dispersion most preferably has particles which have number average diameter dimensions of from 0.1 to 0.75 microns. The dispersion particles may comprise the ascorbic acid in solution within said polymer, or the particles may comprise the ascorbic acid as a solid dispersion within said particles. The dispersion may have the particles comprise the ascorbic acid in solid solution and the water in solution within said polymer, or the particles may comprise the ascorbic acid and water in solution within said polymer.

A method of forming a dispersion of solid particles will be discussed in terms of Vitamin C (ascorbic acid), but this process is applicable to any other water-soluble material or water-dispersible material, with only minor variations which can be readily optimized by one ordinarily skilled in the art. The process comprises adding the ascorbic acid in a water-soluble polymer may comprise the steps of:

a) forming a first solution of ascorbic acid, water and a water soluble (or water-dispersible) polymer, b) mixing the first solution with a second solution of low HLB surface active agent and oil, c) homogenizing the first solution and the second solution to form a mixture of the first solution and second solution, and d) cooling the mixture, solidifying the first solution to form particles dispersed in said oil.

This method may have the homogenizing done at a temperature above 40° C., preferably above 50° C., more preferably above 55° C.

Surface active agents are well known in the chemical arts. Generally, they comprise a compound (including dimers, trimers, oligomers and polymers) which have an oleophilic functionality and a hydrophilic functionality of sufficient strength that the agents will display affinity to both hydrophilic and oleophilic phases from the different segments or sections of the agent. The stability of a dispersion is adjustable and dependent upon the selection of particular surface active agent. The strength or relative strength of the functional portions of the agent may be selected to effect the degree of stability desired or required in the dispersion. The ordinarily skilled chemist, particularly the formulation chemist is aware of the controls effected by appropriate selection of surface active agents. The art usually characterizes the properties of the hydrophilic agents into various capabilities or groups depending upon a range of HLB values. A low HLB for dispersing hydrophilic materials in an oleophilic or lipophilic medium would usually comprise a material having an HLB of less than 12, preferably between 2 and 12, more preferably between 3 and 11, and most preferably between 3 and 10, between 4 and 10, between 3 and 9, and between 4 and 8. One of ordinary skill in the art may merely refer to trade chemical literature or the many texts on surface active agents to select materials within the scope of practice for low HLB materials. The surfactants may be non-ionic, anionic, cationic or Zwitterionic, with both polar and non-polar units.

The water-soluble or water-dispersible polymers useful in the practice of the present invention may comprise any natural or synthetic polymer within that broad class. For example, methacrylates (with the term (meth)acrylate including both acrylic and methacrylic materials) such as polymers having units derived from acrylic acid, acrylamide, methacrylic acid, sodium polyacrylate (e.g., salts of polyacrylates) and copolymers thereof, cellulosic polymers (e.g., carboxymethyl cellulose, methyl cellulose, cationic celluloses, hydroxyethyl cellulose, hydroxypropyl methyl cellulose, methyl ethyl cellulose, and copolymers thereof), polyethylene glycols and copolymers thereof (e.g., with polypropylene glycol etc.), natural or modified natural resins (e.g., gelatin, phthalated gelatin, gum arabic, hydrolyzed collagen, starches, guar gum, xanthan gum, alginates, dextrin, etc.), polyvinyl resins (e.g., polyvinylpyrrolidone, polyvinyl alcohol, polyvinyl ethers, polystyrene copolymers, and copolymers thereof), water-solubilized or water-dispersible polyurethanes (e.g., substituted with acid groups such as carboxylic acid groups or sulfonic acid groups), water-solubilized or water-dispersible ethers (e.g., PEG-100 ether polymer), poly(methylvinyl ether/maleic acid or maleic anhydride copolymer), polyethylenimines, block copolymers, graft copolymers, and other well known water-soluble or water-dispersible polymeric materials.

The water-soluble, water-dispersible materials may be single materials or combinations of materials selected, for example, for their desirable provision in concert with each other. Examples of the wide range of active or target water-soluble material or water-dispersible material ingredients are vitamins, anti-inflammatory agents, anesthetics, analgesics, enzymes, fragrances, UV absorbers (sunscreen agents), antiperspirants, deodorants, pigments, dyes, hydroxy acids (e.g., alpha hydroxy acids, beta hydroxy acids), skin lightening agents, emollients, medications, antibiotics, antifungal agents, repellants, attractants (e.g., pheromones), and the like. The practice of the present invention is particularly beneficial for combining water-soluble/water-dispersible materials within a single dispersion. For example, multiple vitamins may be combined for delivery, vitamins with hydroxy acids, vitamins with fragrance or skin lightening agents, anesthetics with vitamins, emollients, and/or enzymes or anti-inflammatory agents also provide good combinations of materials. The individual materials may be added at separate times at the initial water-soluble material or water-dispersible material addition step, added in sequence, added into separate solutions and then mixed, as desired.

The provision of the dispersions of the present invention has a wide range of utility. It is important to note that, in fact, the compositions of the present invention include or even comprise dispersions, with solid, water-soluble or water-dispersible materials, dispersed within the oleophilic/lipophilic continuous phase. This dispersion may exist in a number of different forms. If the water-soluble material or water-dispersible material is a solid at the ambient temperature, there may be a particle of the water-soluble material or water-dispersible material with the low HLB material altering its properties at the surface of the particle (e.g., by partial dissolution or non-chemical bonding of the hydrophilic segment of the low HLB material, or with a pendant oleophilic segment extending from the particle), forming a coating over the particle (again with the oleophilic segment tending to address the continuous phase, away from the particle). If the water-soluble material or water-dispersible material is a gel, the relative, the relative association of materials may be similar to that of the solid particle of water-soluble material or water-dispersible material, with the water-soluble/water-dispersible polymer thickening or partially encapsulating the water-soluble material or water-dispersible material. If the water-soluble material or water-dispersible material is present as a liquid solution or liquid, the water-soluble/water-dispersible polymer may act as an encapsulant, with the low HLB surface active agent again acting in its orientation with the surface of the encapsulant, just as it was described with respect to particle of the water-soluble material or water-dispersible material, with its lipophilic segment acting to stabilize the particle within the oleophilic, non-aqueous continuous phase.

The preferred water-in-silicone dispersions comprise from about 0.1% to about 10%, preferably from about 0.5% to about 7.5%, more preferably from about 1% to about 5%, of an surface active agent for dispersing the discontinuous aqueous phase into the continuous silicone phase (percentages by weight of the carrier, the non-aqueous continuous phase material). A wide variety of surface active agents can be employed herein to form the preferred water-in-silicone dispersions. Mixtures of surface active agents are also useful. These surface active agents include those selected from the group consisting of silicone surface active agents, non-silicon-containing surface active agents, and mixtures thereof. It is found that surface active agents having an HLB value outside of these ranges can be utilized if they are used in combination with other surface active agents, so to achieve an effective weighted average HLB for the combination that falls within the ranges described in the previous sentence. The abbreviation, "HLB," stands for hydrophilic-lipophilic balance. The HLB system is well known to one of ordinary skill in the art and is described in detail in "The HLB System, A Time-Saving Guide to Emulsifier Selection," ICI Americas Inc., August 1984, which is incorporated herein by reference in its entirety. A wide variety of silicone surface active agents within the low HLB range are useful herein. These silicon surface active agent are typically organically modified organopolysiloxanes. These materials are also known to those skilled in the art as silicone surfactants. Useful silicone surface active agents include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain pendent C2–C30 pendant side chains. Still other useful dimethicone copolyols include materials having various cationic, anionic, amphoteric, and zwitterionic pendant moieties. The groups are selected such that the molecule has an overall molecular weight from about 200 to about 10,000,000. It is recognized that positional isomers of these copolyols can be achieved. Also useful herein, although not strictly classified as dimethicone copolyols, are silicone surface active agents which include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)propylene )oxide sidechains, polydimethylsiloxane polyether copolymers with pendant organobetaine sidechains, polydimethylsiloxane polyethercopolymers with pendant carboxylate sidechains, polydimethylsiloxane polyether copolymers with pendant quaternary ammonium sidechains; and also further modifications of the preceding copolymers containing pendant C2–C30 straight, branched, or cyclic alkyl moieties. Examples of commercially available dimethicone copolyols useful herein sold by Dow Coming Corporation are Dow Corning Registered TM 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the trade name ABIL Registered TM WE-09 (available from Goldschmidt). Cetyl dimethicone copolyol is also commercially available as a mixture with hexyl laurate (and) polyglyceryl-3 oleate (and) cetyl dimethicone and is sold under the trade name ABIL Registered TM WAS-08 also available from Goldschmidt). Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See International Cosmetic Ingredient Dictionary, Fifth Edition, 1993, which is incorporated by reference herein in its entirety. The dimethicone copolyol surface active agents useful herein are further described in U.S. Pat. No. 4,960,764, to Figueroa, Jr. et al., issued Oct. 2, 1990; European Patent No. EP 330,369, to SaNogueira, published Aug. 30, 1989; G. H. Dahms, et al., "New Formulation Possibilities Offered by Silicone Copolyols," Cosmetics & Toiletries, vol. 110, pp. 91–100, March 1995; M. E. Carlotti et at., "Optimization of W/O-S Emulsions And Study Of The Quantitative Relationships Between Ester Structure And Emulsion Properties," J. Dispersion Science And Technology, 13(3), 315–336 (1992); P. Hameyer, "Comparative Technological Investigations of Organic and Organosilicone Emulsifiers in Cosmetic Water-in-Oil Emulsion Preparations," HAPPI 28(4), pp. 88–128 (1991); J. Smid-Korbar et at., "Efficiency and usability of silicone surfactants in emulsions," Provisional Communication, International Journal of Cosmetic Science, 12, 135–139 (1990); and D. G. Krzysik et al., "A New Silicone Emulsifier For Water-in-Oil Systems," Drug and Cosmetic Industry, vol. 146(4) pp. 28–81 (April 1990); which have already been incorporated by reference herein in their entirety. Among the non-silicon-containing surface active agents useful herein are various non-ionic and anionic emulsifying agents such as sugar esters and polyesters, alkoxylated sugar esters and polyesters, C1–C30 fatty acid esters of C1–C30 fatty alcohols, alkoxylated derivatives of C1–C30 fatty acid esters of C1–C30 fatty alcohols, alkoxylated ethers of C1–C30 fatty alcohols, polyglyceryl esters of C1–C30 fatty acids, C1–C30 esters of polyols, C1–C30 ethers of polyols, alkylphosphates, polyoxyalkylene fatty ether phosphates, fatty acid amides, acyl lactylates, soaps, and mixtures thereof. See McCutcheon's, Detergents and Emulsifiers, North American Edition (1986), published by Allured Publishing Corporation; U.S. Pat. No. 5,011,681 to Ciotti et at., issued Apr. 30, 1991; U.S. Pat. No. 4,421,769 to Dixon et at., issued Dec. 20, 1983; and U.S. Pat. No. 3,755,560 to Dickert et at., issued Aug. 28, 1973; these four references are incorporated herein by reference in their entirety. Nonlimiting examples of these non-silicon-containing surface active agents include: polyethylene glycol 20 sorbitan monolaurate (Polysorbate 20), polyethylene glycol 5 soya sterol, Steareth-20, Ceteareth-20, PPG-2 methyl glucose Ceteth- 10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaturate, polyoxyethylene 4 lauryl ether sodium stearate, polyglyceryl-4 isostearate, hexyl laurate, steareth-20, ceteareth-20, PPG-2 methyl glucose ether distearate, ceteth- 10, diethanolamine cetyl phosphate, glyceryl stearate, PEG-100 stearate, and mixtures thereof.

EXAMPLE

A first solution is prepared comprising 5 g of a long-chain (e.g., C 16 or higher) fatty acid monoester of a polyhydric alcohol (e.g., sorbitan monostearate) (surfactant), 35 g of mineral oil and then heated to 60° C. At the same time, 20 g of polyethylene glycol (a water-soluble polymer having a molecular weight of between 1000 and 5000) was dissolved into 20 g deionized water, stirred, and heated to about 60° C. until a clear solution formed. Other materials, if desired, would be conveniently dissolved and added to this solution at this time. While maintaining the 60° C. temperature, 20 g of L-ascorbic acid were dissolved in the solution with stirring. Immediately upon complete dissolution, the aqueous phase was dispersed into the oil phase using a homogenizing device, in this case an ultrasonic homogenizer until fairly uniform. Particles (about 500nm) were formed. The dispersion was cooled to room temperature to form a dispersion of particles in a continuous oil phase. The particles comprised the polymer, ascorbic acid, and water. These three ingredients can be present in a number of different distributions within the particulate phase, depending upon the relative concentrations and the relative rate of cooling. For example, the water and ascorbic acid may approximate a molecular distribution (solution of water in polymer and/or solid solution of ascorbic acid in polymer), may comprise a solution (of water in polymer) and a dispersion of ascorbic acid particles in the solid polymer phase, and may comprise a mix of these different states within the particle. Hydrates or other molecular associations of the water and ascorbic acid may be present within the particle as solutions or dispersions. These dispersions of particles (comprising water, ascorbic acid and polymer) in an oil phase exhibits higher stability than aqueous solutions at both room temperature and elevated temperatures. This higher stability can be achieved without special packaging or special environmental protections (e.g., the absence of oxygen.).

Stability data for this type of product

| Percent L-ascorbic acid remaining | |
| --- | --- |
| 0 months | 24 months |
| 100% | 85% |

L-ascorbic acid dispersion stored at room temperature with room-air head-gas. Percent L-ascorbic acid present assayed by HPLC (high pressure liquid chromatography).

| | Color of Vit C solutions | |
| --- | --- | --- |
| | 0 months | 24 months |
| 20% Vit C as presented in this application | White | Off white to slight yellow |
| 20% Vit C in water | Clear | Very dark brown |

Samples of similar products were stored at room temperature with room-air head-gas.

The high level of storage stability of this product can be readily seen from this example.

Other additives may be present within the composition such as fillers, , powders, thickening agents, chalks, opacifying agents, antioxidants, fumed silica, extracts, and the like, in amounts for example of up to 25% by weight of the composition without detracting from the practice of the invention. The additives may be provided as convenient along with other ingredients.

What is claimed:

1. A dispersion comprising non-aqueous phase containing particles comprising
   a) at least one water-soluble or water-dispersible polymer,
   b) at least one non-polymeric water-soluble material or water-dispersible material comprising ascorbic acid,
   c) water, and
   d) at least one surface active agent having a hydrophilic-lipophilic balance of less than 12.
2. The dispersion of claim 1 wherein said particles have number average diameter dimensions of less than 2 microns, and said at least one surface active agent has a hydrophilic-lipophilic balance of between 2 and 12.
3. The dispersion of claim 1 wherein said particles have number average diameter dimensions of less than 1 micron.
4. The dispersion of claim 1 wherein said dispersion comprises a dispersion of said particles in an oil, and said oil comprises a mineral oil, silicone oil, fluorocarbon oil, or cosmetic oil and said at one surface active agent has a hydrophilic lipophilic balance of between 3 and 9.
5. The dispersion of claim 1 wherein said particles have number average diameter dimensions of from 0.1 to 0.75 microns.
6. The dispersion of claim 1 wherein when said particles are separated from said oil phase.
7. The dispersion of claim 2 wherein said particles comprise said ascorbic acid as a solid dispersion.
8. The dispersion of claim 1 wherein said particles comprise said ascorbic acid as a solid dispersion.
9. The dispersion of claim 1 wherein said particles comprise said ascorbic acid in solid solution within said polymer.
10. The dispersion of claim 1 wherein said particles comprise said ascorbic acid and water in solution within said polymer.
11. A cosmetic composition comprising the dispersion of claim 1 in a carrier medium which does not dissolve said particles.
12. A method of forming a dispersion of solid particles comprinsing a water-soluble material or water-dispersible material comprising ascorbic acid in a water-soluble/water-dispersible polymer comprising the steps of:
    a) forming a first solution of a water-soluble material or water-dispersible material comprising ascorbic acid, water and a water soluble/water-dispersible polymer,
    b) mixing said solution with a second solution of a water in a surface active agent having an HLB less than 12 and oil,
    c) dispersing said first solution and said second solution to form a mixture of said first solution and second solution, and
    d) cooling said mixture, solidifying said first solution to form particles dispersed in said oil.
13. The method of claim 12 wherein said dispersing is done at a temperature above 40° C.
14. The method of claim 12 wherein said dispersing is done at a temperature above 50° C.
15. The method of claim 12 wherein said particles comprise water-soluble polymer, ascorbic acid, and water.
16. The process of claim 12 wherein said particles have number average diameter dimensions of less than 1 micron.
17. The process of claim 12 wherein said particles have number average diameter dimensions of from 0.1 to 0.75 microns and comprise ascorbic acid in solution within said polymer.
18. The process of claim 12 wherein said particles have number average diameter dimensions of from 0.1 to 0.75 microns and comprise ascorbic acid in solid solution within said polymer.
19. The dispersion of claim 1 comprising at least two different water-soluble material or water-dispersible materials within said particles.
20. The dispersion of claim 1 comprising vitamin C and at least one ingredient selected from the group consisting of alphahydroxy acid, betahydroxy acid, fragrances, and skin lightening agents.
21. The dispersion of claim 1 as at least part of a phase in an emulsion.
22. The dispersion of claim 1 as at least part of a phase in a water-in-oil or oil-in-water emulsion.
23. The dispersion of claim 1 wherein said water-soluble or water-dispersible compound comprises at least one compound selected from the group consisting of vitamins, anti-inflammatory agents, anesthetics, analgesics, enzymes, fragrances, UV absorbers (sunscreen agents), antiperspirants, deodorants, pigments, dyes, hydroxy acids, skin lightening agents, emollients, medications, antibiotics, antifingal agents, repallants, and attractants.
24. A composition for application to the skin comprising the dispersion of claim 1.
25. The composition of claim 24 wherein emollients are present with said dispersion.

26. A composition for application to hair comprising the dispersion of claim 1.

27. An emulsion having dispersed therein the dispersion of claim 1.

28. A composition for application to the skin comprising the dispersion of claim 1 and at least one other ingredient outside the particles of said dispersion selected from the group consisting of vitamins, anti-inflammatory agents, anesthetics, analgesics, enzymes, fragrances, UV absorbers, antiperspirants, deodorants, pigments, dyes, hydroxy acids, skin lightening agents, emollients, medications, antibiotics, antifungal agents, repellants, and attractants.

29. The dispersion of claim 1 wherein at least two materials selected from the class consisting of non-polymeric water-soluble material and water-dispersible material are present within said particles.

30. A dispersion in oil comprising a particle phase dispersed in oil, wherein the particle phase comprises:
   a) at least one water-soluble or water-dispersible polymer,
   b) at least one non-polymeric water-soluble material or water-dispersible material comprising ascorbic acid,
   c) water, and
   d) at least one surface active agent having a hydrophilic-lipophilic balance of less than 12.

31. The dispersion of claim 10 wherein said oil comprises a mineral oil, silicone oil, fluorocarbon oil, or cosmetic oil and said at one surface active agent has a hydrophilic lipophilic balance of between 3 and 9.

32. A composition for application to the skin comprising the dispersion of claim 30 and at least one other ingredient outside the particles of said dispersion selected from the group consisting of vitamins, anti-inflammatory agents, anesthetics, analgesics, enzymes, fragrances, UV absorbers, antiperspirants, deodorants, pigments, dyes, hydroxy acids, skin lightening agents, emollients, medications, antibiotics, antifungal agents, repellants, and attractants.

33. A composition for application to the skin comprising the dispension of claim 31 and at least one other ingredient outside the particles of said dispersion selected from the group consisting of vitamins, anti-inflammatory agents, anesthetics, analgesics, enzymes, fragrances, UV absorbers, antiperspirants, deodorants, pigments, dyes, hydroxy acids, skin lightening agents, ernollients, medications, antibiotics, antifungal agents, repellants, and attractants.

* * * * *

UNITED STATES PATENT AND TRADEMARK OFFICE
CERTIFICATE OF CORRECTION

PATENT NO. : 6,103,267
DATED : August 15, 2000
INVENTOR(S) : Mitchnick et al.

It is certified that error appears in the above-identified patent and that said Letters Patent is hereby corrected as shown below:

<u>Column 1,</u>
Line 45, delete "bum" and insert -- burn --, therefor.

<u>Column 9,</u>
Line 39, delete "fillers, ," and insert -- fillers, -- therefor.

<u>Column 10,</u>
Line 15, claim 12, delete "comprinsing" and insert -- comprising -- therefor.
Line 63, claim 23, delete "antifingal" and insert -- antifungal -- therefor.

<u>Column 12,</u>
Line 1, claim 31, delete "claim 10" and insert -- claim 30 -- therefor.
Line 21, claim 33, delete "ernollients" and insert -- emollients -- therefor.

Signed and Sealed this

Seventh Day of August, 2001

*Attest:*

NICHOLAS P. GODICI
*Attesting Officer*     Acting Director of the United States Patent and Trademark Office